March 22, 1966 H. A. M. VERSCHUREN Plant Pat. 2,609
ROSE PLANT
Filed Dec. 29, 1964
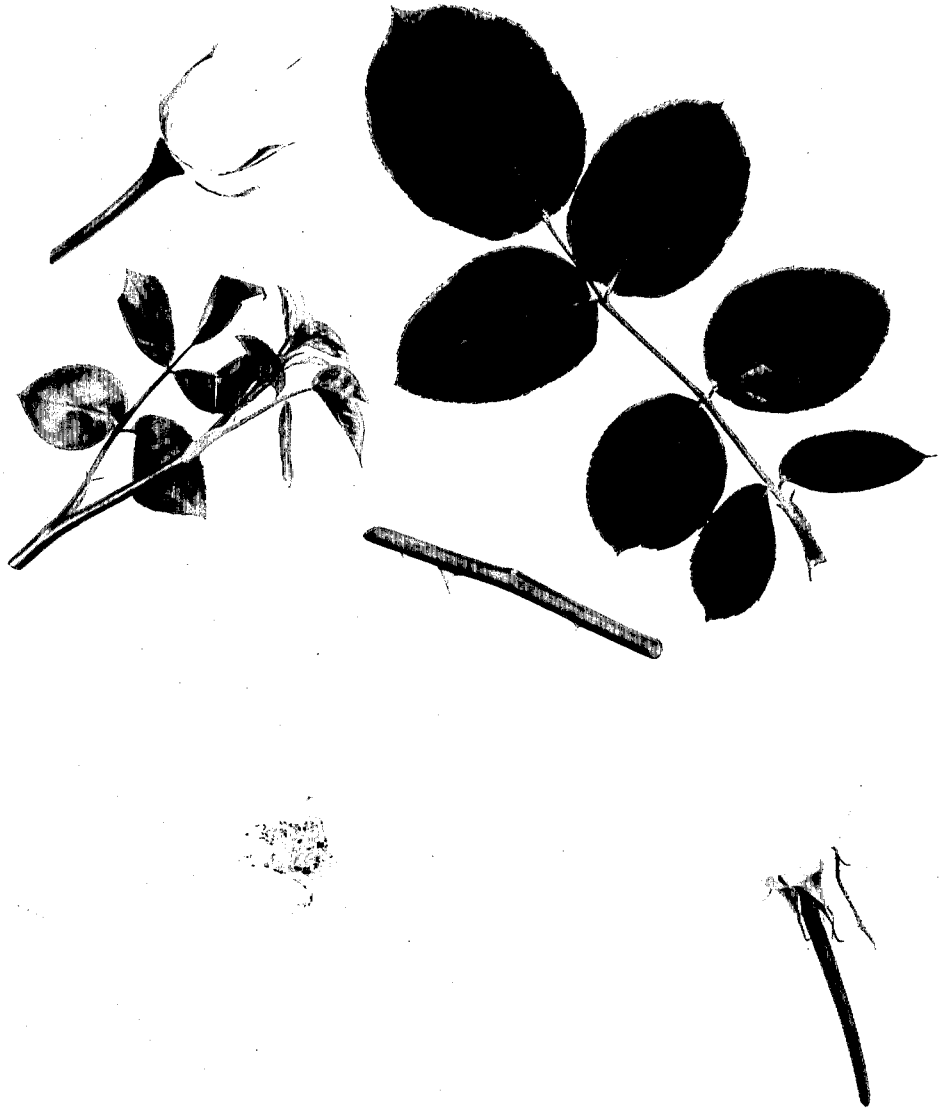
Inventor.
H. A. M. Verschuren
By: Robb & Robb
Attorneys.

United States Patent Office

Plant Pat. 2,609
Patented Mar. 22, 1966

2,609
ROSE PLANT

Hendrikus Antonie Maria Verschuren, Haps, Netherlands, assignor to Jackson & Perkins Company, Newark, N.Y., a corporation of New York Filed Dec. 29, 1964, Ser. No. 422,105
1 Claim. (Cl. Plt.—15)

The present invention relates to a new and distinct variety of rose plant of the hybrid tea class, which was originated by me by crossing the variety "Peace" (U.S. Plant Patent No. 591) with the variety "Golden Rapture" (unpatented).

The primary objective of this breeding was to produce a new rose variety generally corresponding to the parent variety "Peace," but which bears flowers of a deeper color than those of this parent. This objective was fully achieved, along with other desirable improvements, as evidenced by the following unique combination of characteristics which are outstanding in the new variety and which distinguish it from its parent, as well as from all other varieties of which I am aware:

(1) A similarity in growth and flower form to the variety "Peace" (U.S. Plant Patent No. 591) but without the usual colored petal edges of the flowers of "Peace,"

(2) A heavier flower production than that of the parent variety "Peace"; and (3) A distinctive, attractive and uniform yellow color of the flowers, corresponding to Light Chalcedony Yellow, with the edges of the flower petals lightly overcast with Citron Yellow.

Asexual reproduction of the new variety by budding, as performed in the Netherlands, as well as at Newark, New York, and Pleasanton, California, U.S.A., shows that the foregoing characteristics and distinctions come true to form and are established and transmitted through succeeding propagations.

The accompanying drawings show typical specimens of the vegetative growth and flowers of my new variety in different stages of development and as depicted in color as nearly true as it is reasonably possible to make the same in a color illustration of this character.

The following is a detailed description of the new variety, with color terminology in accordance with Ridgway's Color Standards and Nomenclature:

Parentage: Seedling.
*Seed parent.*—"Peace."
*Pollen parent.*—"Golden Rapture."
Classification:
*Botanic.*—Hybrid tea.
*Commercial.*—Hybrid tea.

*Flower*

(Observations made from specimens grown outdoors at Newark, New York, U.S.A., in the late morning during the early part of the month of July.)

Blooming habit: Recurrent—continuous.
Bud:
*Size.*—Large.
*Form.*—Ovoid; is not affected by wet or hot weather.
*Color.*—When sepals first divide—Empire Yellow, Plate 4. When petals begin to unfurl—Pinard Yellow, Plate 4, lightly overcast with Empire Yellow, Plate 4. When half-blown: Inside of petals—Pinard Yellow, Plate 4, lower half of petal, with upper half of petal Barium Yellow, Plate 16, and edge of petal overcast with Picric Yellow, Plate 4; reverse of petals—Napthalene Yellow, Plate 16, very lightly overcast with Picric Yellow, Plate 4.
*Sepals.*—Branched; curl back when petals begin to unfurl. Color: Inside—Kildare Green, Plate 31; outside—Bice Green, Plate 17.
*Calyx.*—Color — Light Elm Green, Plate 17. Shape — apple. Size — large. Aspect — smooth. Odor when rubbed—none.
*Peduncle.*—Length — medium. Aspect — rough. Strength—erect; heavy. Color—Light Elm Green, Plate 17.
*Opening.*—Opens up well; is not affected by adverse weather conditions.

Bloom:
*Size.*—Large. Average size when fully expanded—5½ inches.
*Borne.*—Both singly and several together; very productive in bloom.
*Stems.*—Long; strong.
*Form (when fully open).*—Cupped and full. Permanence—retains its form to the end.
*Petalage.*—Double (full but open center). Number of petals under normal conditions—from 35 to 40.
*Color.*—Center of flower—Empire Yellow, Plate 4. Outer petals—Pale Chalcedony Yellow, Plate 17, with edge of petal lightly overcast with Citron Yellow, Plate 16. Base of petals (aiglet)—Picric Yellow, Plate 4. Inside of petals—Light Chalcedony Yellow, Plate 17, with edge of petal lightly overcast with Citron Yellow, Plate 16. Reverse of petals—Napthalene Yellow, Plate 18, very lightly overcast with Pale Chalcedony Yellow, Plate 17. General tonality from a distance—Light Chalcedony Yellow, Plate 17, slightly overcast with Empire Yellow, Plate 4.
*Discoloration.*—General tonality at end of first day—Light Chalcedony Yellow, Plate 17, lightly overcast with Pale Chalcedony Yellow, Plate 17. Second day—Light Chalcedony Yellow, Plate 5, lightly overcast with Pale Chalcedony Yellow, Plate 17. Third day—Pale Chalcedony Yellow, Plate 17, with edge of petal lightly overcast with Citron Yellow, Plate 16.

Petals:
*Texture.*—Thick; is not affected by wet or hot weather.
*Appearance.*—Inside—satiny. Outside—shiny.
*Form.*—Oval.
*Arrangement.*—Imbricated (regularly arranged shingle-like).
*Petaloids in center.*—Few; large.
*Persistence.*—Drop off cleanly.
*Fragrance.*—Moderate. Nature—tea (average hybrid tea scent).
*Lasting quality.*—On the plant—long. As cut flower—long.

*Genital organs*

Stamens, anthers: Medium size; many; regularly arranged around styles. Color—Mustard Yellow, Plate 16.
Stamens, filaments (threads): Long. Color—Picric Yellow, Plate 4.
Pollen: Color—Massicot Yellow, Plate 16.
Styles: Bunched; uneven length; short; thin.
Stigmas: Color—Amber Gold, Plate 16.
Ovaries: All enclosed in calyx.
Hips: None.
Seeds: None.

*Plant*

Form: Bush.
Growth: Vigorous; upright and branching.
Foliage: Compound of 5 to 7 leaflets.
*Size.*—Large.
*Quantity.*—Abundant.
*Color.*—New foliage: Upper side—Lettuce Green, Plate 5, with outer edge of petal lightly overcast with Hay's Russet, Plate 14; under side—Cosse Green, Plate 5, overcast lightly with Vinaceous-Rufous, Plate 14. Old foliage: Upper side—Varley's Green, Plate 18; under side—Light Elm Green, Plate 17.
*Shape.*—Oval pointed.
*Texture.*—Upper side—glossy. Under side—smooth.
*Ribs and veins.*—Prominent.
*Edge.*—Serrated (saw-toothed).
*Serration.*—Both double and single; small.
*Leaf stem.*—Color—Light Bice Green, Plate 17. Under side—prickly.
*Stipules.*—Long; bearded.
Wood:
*New wood.*—Color—Lettuce Green, Plate 5. Bark—smooth.
*Old wood.*—Color—Biscay Green, Plate 17. Bark—smooth.

Thorns:
*Thorns.*—Quantity: On main stalks from base—few; on laterals from stalk—few. Form—narrow base; medium length; hooked downward. Color (when young)—Chalcedony Yellow, Plate 17. Position—irregular.
*Prickles.*—Quantity: On main stalks—none; on laterals—none.
*Short needles.*—Quantity: On main stalks—none; on laterals—none.

I claim:

A new and distinct variety of rose plant of the hybrid tea class, substantially as herein shown and described, characterized particularly as to novelty by the unique combination of a similarity in growth and flower form to the variety "Peace" (U.S. Plant Patent No. 591) but without the usual colored petal edges of the flowers of "Peace," a heavier flower production than that of the parent variety "Peace," and a distinctive, attractive and uniform yellow color of the flowers, corresponding to Light Chalcedony Yellow, with the edges of the flower petals lightly overcast with Citron Yellow.

No references cited.

ABRAHAM G. STONE, *Primary Examiner.*